(12) United States Patent
Park et al.

(10) Patent No.: US 11,607,474 B2
(45) Date of Patent: Mar. 21, 2023

(54) METHOD FOR PREPARING OF NERVE CONDUIT USING BIO-PRINTING TECHNOLOGY AND THE NERVE CONDUIT PREPARED BY THE SAME

(71) Applicants: Korea University Research and Business Foundation, Seoul (KR); Korea Institute of Science and Technology, Seoul (KR)

(72) Inventors: Jong Woong Park, Seoul (KR); Young Mee Jung, Seoul (KR); Soo Hyun Kim, Seoul (KR); Justin Jihong Chung, Seoul (KR)

(73) Assignees: Korea University Research and Business Foundation, Seoul (KR); Korea Institute of Science and Technology, Seoul (KR)

( * ) Notice: Subject to any disclaimer, the term of this patent is extended or adjusted under 35 U.S.C. 154(b) by 489 days.

(21) Appl. No.: 16/875,107

(22) Filed: May 15, 2020

(65) Prior Publication Data
US 2020/0376167 A1    Dec. 3, 2020

(30) Foreign Application Priority Data
Mar. 19, 2019   (KR) .......................... 10-2019-0030849

(51) Int. Cl.
    A61L 27/38        (2006.01)
    A61L 27/26        (2006.01)
    A61L 27/54        (2006.01)

(52) U.S. Cl.
    CPC ........... *A61L 27/3878* (2013.01); *A61L 27/26* (2013.01); *A61L 27/54* (2013.01); *A61L 2300/252* (2013.01); *A61L 2430/32* (2013.01)

(58) Field of Classification Search
    None
    See application file for complete search history.

(56) References Cited

FOREIGN PATENT DOCUMENTS

| | | |
|---|---|---|
| CN | 109172036 A | 1/2019 |
| JP | 2009-045221 A | 3/2009 |
| JP | 2015-533094 A | 11/2015 |
| KR | 10-2011-0110667 A | 10/2011 |
| KR | 10-2018-0125776 A | 11/2018 |

OTHER PUBLICATIONS

Huang et al., "The Differentiation Stage of Transplanted Stem Cells Modulates Nerve Regeneration", 2017, Scientific Reports, vol. 7, Article No. 17401, pp. 1-12.*

* cited by examiner

*Primary Examiner* — Robert A Wax
*Assistant Examiner* — Randeep Singh
(74) *Attorney, Agent, or Firm* — NSIP Law (57) ABSTRACT

The present invention relates to a method for preparing of a nerve conduit using bio-printing technology and a nerve conduit prepared by the same, and it can easily prepare a nerve conduit by simulating a nerve bundle and nerve tissue, and the like, by three-dimensionally printing bio-ink comprising a neuronal regeneration material on one side of a porous polymer scaffold.

13 Claims, 5 Drawing Sheets

METHOD FOR PREPARING OF NERVE CONDUIT USING BIO-PRINTING TECHNOLOGY AND THE NERVE CONDUIT PREPARED BY THE SAME

TECHNICAL FIELD

The present invention relates to a method for preparing of a nerve conduit using bio-printing technology and a nerve conduit prepared by the same.

BACKGROUND ART

When peripheral nerves are damaged by wounds, a method of anastomosis of the cut surface of the cut nerves directly is performed. However, it is almost impossible to directly anastomose most of nerves accurately. When direct end-to-end anastomosis is impossible, autogenous nerve graft is performed to restore its function. However, the autogenous nerve graft has a disadvantage that it is difficult to match the thickness and shape of the nerve tissue at the injured site and the nerve tissue to be transplanted, and there is a limit to nerves which can be harvested. In addition, the deterioration and loss of critical function may be caused even in the area where the grafting nerves are harvested. Therefore, when a nerve defect site occurs, a nerve conduit is used as a method for restoring its function.

A nerve conduit is a connecting pipe which connects both ends of a missing nerve and plays a guide role to the regenerating nerve, and it fixes both ends of the severed nerve in the nerve conduit and incudes connection of the nerve into the conduit. When the nerve conduit is used, it is possible to prevent penetration of scar tissue that interferes with nerve regeneration and induce the nerve generation in the correct direction. In addition, the nerve conduit provides advantages of maintaining nerve regeneration promoting substances secreted from the nerve itself and preventing substances that interfere with regeneration from entering the conduit.

On the other hand, a non-degradable silicone tube was used as the first nerve conduit. However, there is a problem that remains in the body even after the nerve is regenerated, causing chronic inflammation, calcification of silicone and pain by pressing the regenerated nerved, and it is cumbersome to remove the tube by reoperation after the nerve is completely restored.

Recently, cell printing technology capable of precisely positioning various cells in a desired position, and the like, have been developed. More specifically, research to develop artificial tissue which can replace damaged organs or tissue of a human body by printing scaffolds that can support cells and growth factors that support cell growth, using 3D bio-printing technology has been actively progressed.

However, when 3D bio-printing is applied when manufacturing a nerve conduit, tissue to guide to create damaged tissue of a printed nerve conduit is required, but there was no tissue like that and there was a difficulty such as creating a guide tissue that allows the nerve to grow in the conduit.

PRIOR ART

Patent Literature

Japanese Patent Publication No. 2009-45221

DISCLOSURE

Technical Problem

The present invention is to provide a method for preparing of a nerve conduit which can prepare a nerve conduit by printing bio-ink comprising a neuronal regeneration material on one side or both sides of a porous polymer scaffold, to solve the aforementioned problems.

In addition, it is to provide a nerve conduit prepared by the method for preparing of a nerve conduit.

Technical Solution

To achieve the above objects, in one example, the present invention provides, a method for preparing of a nerve conduit comprising, printing bio-ink comprising neuroregenerative materials on one side or both sides of a porous polymer scaffold using a three-dimensional bio-printer (3D bio-printer) in which a three-dimensional bio-ink is printed; and preparing a nerve conduit by wrapping the polymer scaffold in a conduit form, wherein the bio-ink comprises at least one selected from the group consisting of hydrogel, neuroregenerative factors and cells.

In addition, in one example, the present invention provides a nerve conduit prepared by the method for preparing of a nerve conduit.

Advantageous Effects

According to the method for preparing of a nerve conduit of the present invention, a nerve conduit can be easily prepared by stimulating a regenerating axons and nerve tissue by three-dimensional printing bio-ink comprising neuroregenerative materials on one side or both sides of a porous polymer scaffold free of material exchange from external environment.

In particular, by using three-dimensional printing during preparation of a nerve conduit, neuroregenerative materials constituting a nerve conduit, and the like can be easily arranged and mixed.

In addition, by providing neuroregenerative materials and neurons, and the like for the nerve conduit prepared, neural regeneration in the nerve defect area is maximized to shorten the nerve regeneration period, and finally, it is possible to overcome limitations of the current nerve conduit graft through functional recovery of the nerve regeneration site.

Furthermore, a nerve conduit having a patient-specific configuration in consideration of characteristics of different diameters and lengths for each patient can be printed, and it can be applied as a patient-specific bioprinting nerve conduit which is patient-friendly and immune response is optimized in.

DETAILED DESCRIPTION OF THE EMBODIMENTS

The present invention may be applied by various modifications and may have various examples, and therefore, specific examples will be illustrated in the drawings and described in detail in the detailed description.

However, these are not intended to limit the present invention to specific embodiments, and should be understood to include all modifications, equivalents or substitutes included in the spirit and scope of the present invention. In the description of the present invention, when it is determined that a detailed description of related known technology may obscure the gist of the present invention, the detailed description will be omitted.

The terms used in the present application are only used to describe specific examples and are not intended to limit the present invention. Singular expressions include plural expressions unless clearly indicated otherwise in the context.

In the present invention, terms such as 'comprise' or 'have' are intended to designate the existence of features, numbers, steps, operations, components, parts or combinations thereof described in the specification, and should be understood that it does not preclude the possibility of the existence or addition of one or more of other features, numbers, steps, operations, components, parts, or combinations thereof.

The present invention relates to a method for preparing of a nerve conduit using bio-printing technology and a nerve conduit prepared thereby.

The present invention, in one example, provides, a method for preparing of a nerve conduit, comprising printing bio-ink on one side or both sides of a porous polymer scaffold using a three-dimensional bio-printer (3D bio-printer); and preparing a nerve conduit by wrapping the porous polymer scaffold in which the bio-ink is printed in a conduit form;

wherein the bio-ink comprises at least one selected from the group consisting of hydrogel, neuroregenerative factors and cells.

In addition, the present invention, in one example, provides a nerve conduit prepared by the method for preparing of a nerve conduit.

Prior to description, among terms used in the present invention, "bio-printing" mean using three-dimensional accurate bio-ink deposition (e.g., hydrogel, cell solution, cell-containing gel, cell suspension, cell concentrate, multicellular aggregate, multicellular body, etc.) through a computer-aided, three-dimensional prototyping device (e.g., three-dimensional printer) and common methodology. More specifically, in the present invention, three-dimensional printing may be performed by discharging a material capable of forming nerve tissue in a nerve conduit prepared using a bio-plotter from a nozzle and stacking it on a porous polymer scaffold.

Hereinafter, the method for preparing of a nerve conduit and the nerve conduit prepared thereby according to the present invention will be described in detail.

Figure 1:
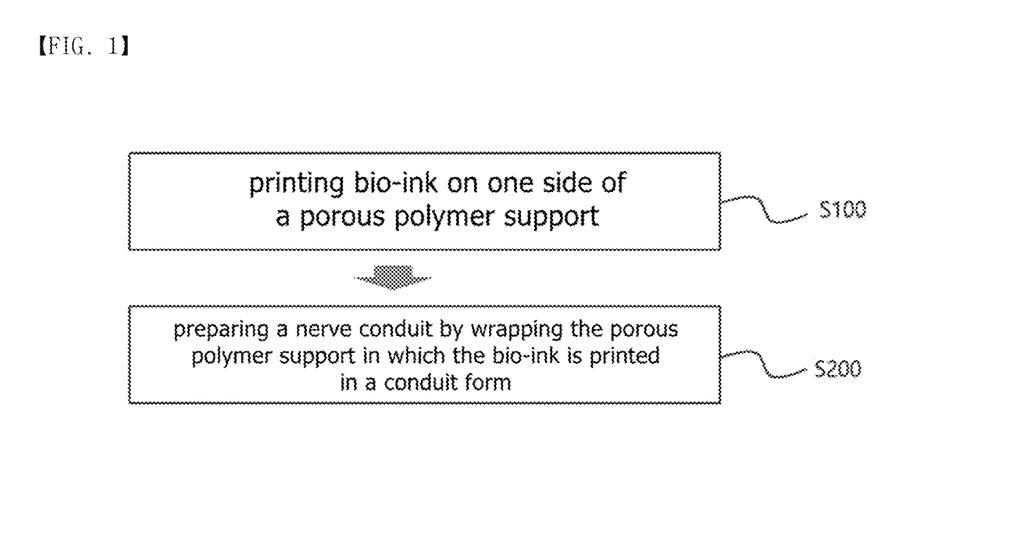
FIG. 1 is a flow chart showing the method for preparing of a nerve conduit of the present invention.
Figure 2:
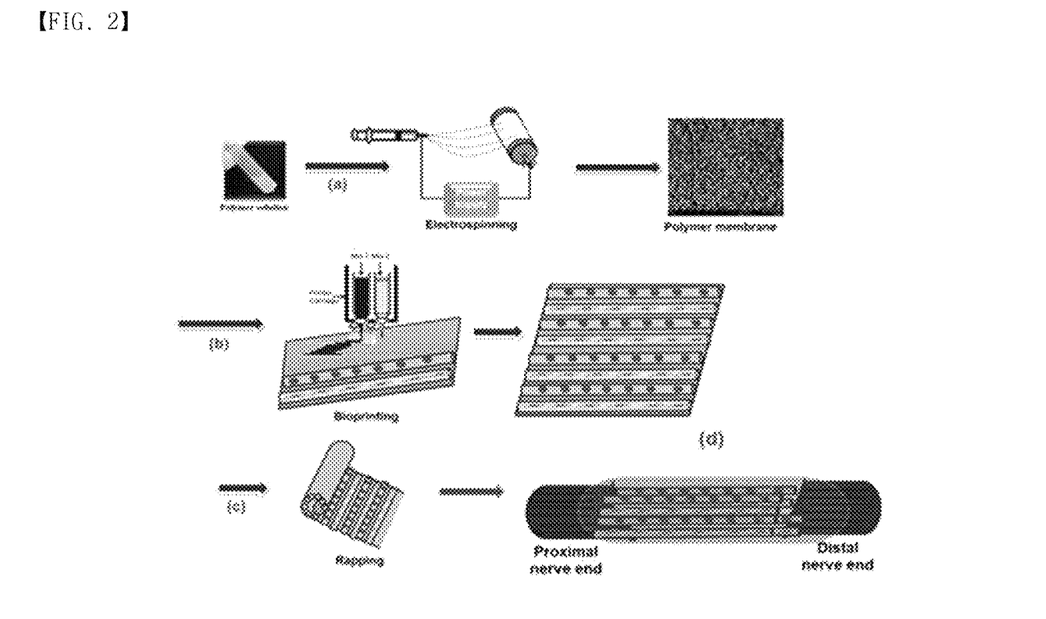
FIG. 2 is a drawing schematically showing the steps of the method for preparing of a nerve conduit of the present invention.

FIG. 1 is a flow chart showing the method for preparing of a nerve conduit of the present invention, and FIG. 2 is a drawing which schematically shows steps of the method for preparing of a nerve conduit of the present invention.

Referring to FIG. 1 and FIG. 2, printing bio-ink on one side of a porous polymer scaffold using a three-dimensional bio-printer (S100); and preparing a nerve conduit by wrapping the porous polymer scaffold in which bio-ink is printed in a conduit form (S200); are comprised.

The porous polymer scaffold may be in a sheet form obtained by electrospinning a spinning solution in which a biocompatible polymer and a solvent are mixed.

On the other hand, in the present invention, to prepare a porous polymer scaffold, a biocompatible polymer and a solvent are mixed to prepare a spinning solution and the spinning solution is electrospun to prepare a porous polymer scaffold.

Herein, "biocompatible polymer" may mean a polymer which is biocompatible and biodegradable. More specifically, the biocompatible polymer may comprise at least one polymer selected from the group consisting of polycaprolactone (PCL), polylactide (PLA), polyglycolide, polyurethane (PU), polydioxanone (PDO), polyethylene glycol (PEG), poly(N-isopropyl acrylamide-co-acrylic acid), polyvinyl alcohol (PVA), polystyrene (PS) and polyester, and preferably, it may be polycaprolactone (PCL).

In addition, the solvent used in electrospinning may be at least one selected from the group consisting of HFIP (Hexafluoro-2-propanol), DMAc (N,N-Dimethyl acetoamide), DMF (N,N-Dimethylformamide), NMP (N-methyl-2-pyrrolidinone), DMSO (dimethyl sulfoxide), THF (tetrahydrofuran), EC (ethylene carbonate), DEC (diethyl carbonate), DMC (dimethyl carbonate), EMC (ethyl methyl carbonate), PC (propylene carbonate), water, acetic acid, formic acid, chloroform, dichloromethane, acetone and isopropyl alcohol.

A common electrospinning device may be used to prepare a porous polymer scaffold. Accordingly, there is no particular limitation, and an electrospinning device capable of applying a general high voltage (5 to 50 kV) may be widely used. As one aspect, the electrospinning may discharge the polymer solution to an electrospinning collection unit to prepare a porous polymer scaffold having a fibrous structure. In addition, considering the concentration of the polymer solution to be prepared when electrospinning and the diameter of the nerve conduit, the discharging rate and voltage may be controlled. As one example, the discharging rate may be 0.1 to 5.0 ml/h, and the voltage of 1 to 50 kV may be applied.

The porous polymer scaffold prepared in this way may be in a sheet form with an average thickness of 10 to 1000 nm, and may be in a sheet from with an average thickness of 1 nm to 500 nm. More specifically, the average thickness of the porous polymer scaffold may be in a range of 10 to 1000 nm, in a range of 20 to 900 nm, in a range of 40 to 800 nm, in a range of 70 to 700 nm, in a range of 100 to 600 nm, in a range of 150 to 500 nm, in a range of 200 to 400 nm, or in a range of 250 to 350 nm, and as one example, the porous polymer scaffold may be 300 nm at average.

Furthermore, the porous polymer scaffold may comprise a pore with an average diameter of 1 nm to 500 nm, and it may be 5 nm to 450 nm, 10 nm to 400 nm, 20 nm to 350 nm, 30 nm to 300 nm, 40 nm to 250 nm, 50 nm to 200 nm, 60 nm to 150 nm, or 70 nm to 100 nm. As a specific aspect, when the pore of the porous polymer scaffold is less than 1 nm, the exchange of the body fluid between the inside and outside of the nerve conduit is not easily performed, and when it is over 500 nm, the pore of the scaffold is too large, and therefore there may be a problem of leaking of bio-ink to the outside of the conduit.

On the other hand, the prepared porous polymer scaffold may further comprise coating protein such as collagen to increase the adhesion rate with bio-ink to be described below.

Then, for promoting nerve axonal regeneration for nerve regeneration on one side or both sides of the porous polymer scaffold, bio-ink comprising a neuroregenerative material capable of forming nerve tissue may be printed using a 3D printing method. For example, the bio-ink comprising a neuroregenerative material may comprise at least one selected from the group consisting of hydrogel, neuroregenerative factors and neurons.

More specifically, the printing bio-ink may print bio-ink to form a plurality of lines in the axial direction. Herein, "one direction" may mean the axial direction of a conduit to be prepared, and as one example, it may mean the longitudinal direction of a nerve conduit.

In addition, a nerve conduit may be prepared by wrapping the porous polymer scaffold in which bio-ink is printed in a conduit form (See FIGS. 3A to 3E).

The bio-printed porous polymer scaffold may be rolled from the end to have a diameter equal to or slightly larger than the thickness of the nerve to be implanted to prepare a cylindrical conduit. The conduit may be wrapped so that the average diameter is 0.5 mm to 20 mm. On the other hand, the nerve conduit may be applied for central nerves or peripheral nerves, and the size of the diameter to be applied for central nerves or peripheral nerves may be different. In other words, it may be wrapped by a diameter depending on the application site.

The preparing a nerve conduit may wrap the nerve conduit so as to have any one of a tubular form, a winding form and a fiber bundle form, and as other aspect, the preparing a nerve conduit may comprise preparing a plurality of porous polymer scaffolds in which bio-ink is printed and stacking the plurality of porous polymer scaffolds; and wrapping the stacked plurality of porous polymer scaffolds in a multi-pipe form.

Moreover, as other aspect, after the preparing a nerve conduit, wrapping a plurality of nerve conduits in a multi-pipe form by surrounding them with a porous polymer scaffold may be further comprised.

Figure 3A:
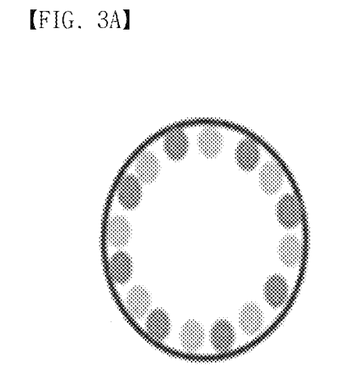
FIGS. 3A to 3E are drawings showing various examples of wrapping a porous polymer scaffold in a conduit form.
Figure 3B:
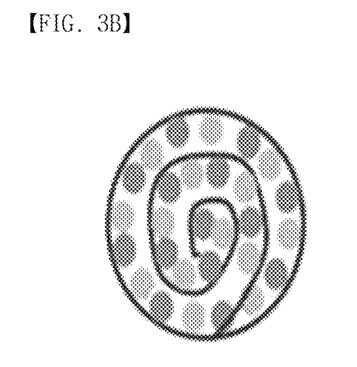
Figure 3C:
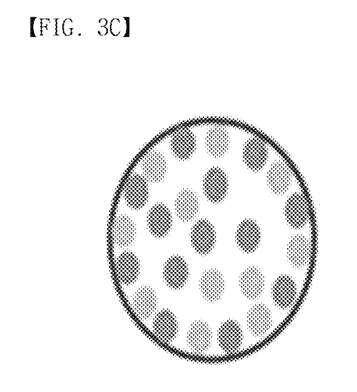
Figure 3D:
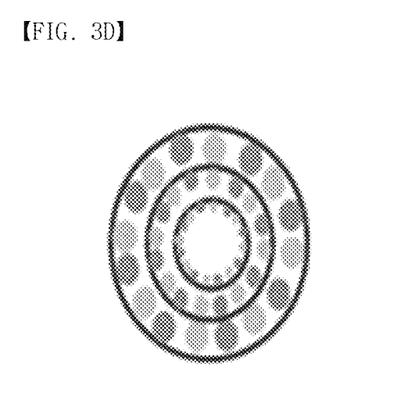
Figure 3E:
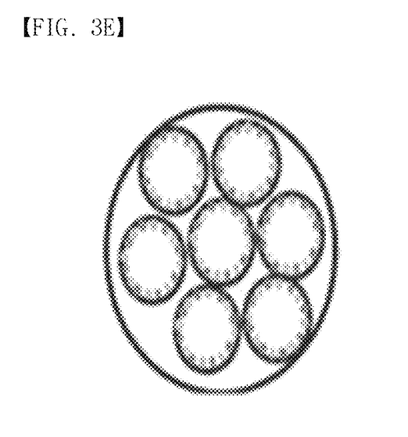

For example, it is possible to prepare a conduit to form a space in the center by making bio-ink form only one layer (FIG. 3A), and it is possible to wrap so that several layers are wrapped in a snail shape so that the inside is filled (FIG. 3B). In addition, when the bio-ink is stacked in several layers, the inside of the conduit may consist of a pipe filled with several lines of bio-ink and a pore between them (FIG. 3C). Moreover, membranes in which bio-ink is printed in one layer may be stacked in multiple layers and then wrapped at once (FIG. 3D), and the multiple structure in which several membranes are wrapped may be finally wrapped to produce a conduit (FIG. 3E).

The hydrogel may comprise at least one selected from the group consisting of polyethylene glycol (PEG), polyethylene oxide (PEO), polyhydroxyethyl methacrylate (PHEMA), polyacrylic acid (PAA), polyvinyl alcohol (PVA), poly(N-isopropyl acrylamide) (PNIPAM), polyvinyl pyrrolidone (PVP), polylactic acid (PLA), polyglycolic acid (PGA) and polycaprolactone (PCL), gelatin, alginate, carrageenan, chitosan, hydroxyalkyl cellulose, alkyl cellulose, silicone, gum, agar, carboxyvinyl copolymers, polydioxolan, polyacrylacetate, polyvinyl chloride, collagen, fibrin, Matrigel, gelatin methacrylate (GelMA) and maleic anhydride/vinyl ether.

Furthermore, the bio-ink may comprise hydrogel, and the hydrogel may further comprise decellularized extracellular matrix (dECM) powders of 5% by weight or less, based on the total weight of the bio-ink composition. As one example, the decellularized extracellular matrix powders may be comprised in an amount of 1% by weight based on the total weight of the bio-ink. For example, the decellularized extracellular matrix may help neurons better differentiate and engraft in normal cells.

In addition, the neuroregenerative factor may be at least one selected from the group consisting of fibroblast growth factor (FGF), bone morphogenetic proteins (BMPs), granulocyte colony-stimulating factor (G-CSF), granulocyte-macrophage colony-stimulating factor (GM-CSF), epidermal growth factor (EGF), growth differentiation factor (GDF), insulin-like growth factor (IGF), interleukin (IL), migration-stimulating factor (MSF), macrophage-stimulating protein (MSP), neurotrophin (NGF), platelet-derived growth factor (PDGF), transforming growth factor (TGF), vascular endothelial growth factor (VEGF) and neurotrophic factor family (NTF).

In addition, the cell may be at least one selected from the group consisting of neurons and stem cells.

More specifically, the neuron may be at least one of cortical neuron, hippocampal neuron, astrocyte, oligodendrocyte, sensory neuron such as microglia and dorsal root ganglia neuron, motorneuron, schwann cell, and satellite cell, and the stem cell may be at least one selected from the group consisting of bone marrow-derived mesenchymal stem cell, tonsil-derived mesenchymal stem cell, embryonic stem cell, iPS and neural stem cell, neural crest cell, neuroblast, gingiva-mesenchymal stem cell, and adipose-derived stem cell.

Not limited thereto, it may be preferably a schwann cell. In the present invention, "schwann cell" plays a role of helping neural regeneration. Attaching this schwann cell to a nerve conduit and connecting the nerve conduit in which the schwann cell is attached to a damaged peripheral or central nerve may promote axonal regeneration.

As a specific aspect, the bio-ink may comprise a first bio-ink comprising at least one selected from the group consisting of hydrogel and neuroregenerative factors; and a second bio-ink comprising at least one selected from the group consisting of hydrogel and neurons. More specifically, the first bio-ink may comprise neurons, neuroregenerative factors and hydrogel, and the second bio-ink may comprise stem cells, neuroregenerative factors and hydrogel. As a specific aspect, the neuroregenerative factors comprised in the first bio-ink and the second bio-ink, respectively, may be different kinds of neuroregenerative factors each other.

Meanwhile, the neuron or stem cell may be comprised in a range of 0.5 to $50 \times 10^6$ cells/ml, and may be comprised in an amount of 0.6 to $40 \times 10^6$ cells/ml, 0.7 to $30 \times 10^6$ cells/ml, 0.8 to $20 \times 10^6$ cells/ml, 0.9 to $10 \times 10^6$ cells/ml, 1.0 to $5 \times 10^6$ cells/ml, or $2 \times 10^6$ cells/ml.

In addition, the bio-ink forms a nerve bundle in a nerve conduit, and may comprise a neuroregenerative material, and as described above, may comprise at least one selected from the group consisting of hydrogel, neuroregenerative factors and cells, and may be printed so as to have a diameter in a range of 10 to 1000 nm.

Furthermore, the three-dimensional bio-printer may comprise at least two of printing nozzles, and the first bio-ink and the second bio-ink may be printed by printing nozzles separated respectively.

In other words, the three-dimensional bio-printer may print lines to be printed by different materials each other using a multi-nozzle. In addition, the lines printed by the bio-ink may be printed as one line or multiple lines on one side of the porous polymer scaffold. For example, when the first bio-ink and the second bio-ink are discharged from separated nozzles, an effect of hydrogel on neuroregenerative factors or neurons may be independently confirmed, and the neuron bundle and extracellular matrix may be arranged according to their characteristics, respectively, and printed.

In addition, physical properties of hydrogel suitable to neuroregenerative factors and neurons may be controlled, and a paracrine effect of the neuroregenerative factor may be provided for neurons printed from separated nozzles.

Then, applying an adhesive for biological tissue on the surface of the nerve conduit prepared in the preparing a nerve conduit may be further comprised. Specifically, a cylindrical nerve conduit may be produced through a wrapping process, and then, an adhesive for biological tissue may be applied so that the wrapped part does not loosen. As other aspect, the prepared nerve conduit may be fixed by a suture or mechanical device.

As the adhesive for biological tissue, at least one selected from the group consisting of fibrin glue, gelatin glue, polyurethane-based adhesives and cyanoacrylate-based adhesives may be used.

By the aforementioned method for preparing of a nerve conduit, a nerve conduit may be easily prepared, and the nerve conduit may be for central nerve or peripheral nerve regeneration, and the prepared nerve conduit may be transplanted to a damaged nerve site and provide a nerve regeneration method, and the like.

Hereinafter, the present invention will be described by the following examples. However, the examples are intended to specifically illustrate the present invention, but the scope of the present invention is not limited by the following examples.

EXAMPLE

Example 1. Preparation of a Nerve Conduit Using Bio-Printing Technology-1

Step 1: Preparation of a Porous Polymer Scaffold

PLCL/HFIP polymer solution of 0.05 g/ml (5 wt. %) which PLCL polymers (poly(L-lactide-co-caprolactone)) were dissolved in HFIP (1,1,1,3,3,3-hexafluoro-2-propanol) was prepared.

Then, the polymer solution was added to a 5 ml glass syringe with a metal needle, and was electrospun on a mandrel at a feed rate of 0.1 ml/hr for 12 hours while applying 21 kV with a high voltage DC power supply.

Then, the distance from the needle end to the mandrel was 20 cm. Through the electrospinning, a porous polymer scaffold having a diameter of 1.5 mm and a thickness of 300 μm was prepared. The prepared porous polymer scaffold was placed in a vacuum at a room temperature for a day to remove the residual solution. Then, the cylindrical scaffold was used by cutting in a sheet form.

Step 2: Bio-Ink Printing on One Side of the Porous Polymer Scaffold

Figure 4:
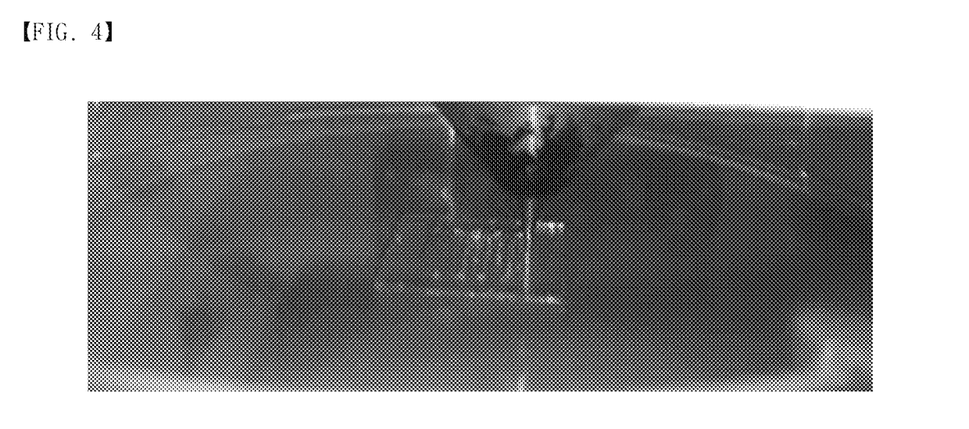
FIG. 4 is a drawing showing the process of printing bio-ink on one side of a porous polymer scaffold line by line in an example.

On one side of the porous polymer scaffold, bio-ink was printed using three-dimensional printing. In the example of FIG. 4, it is a drawing which shows the process of printing bio-ink on one side of the porous polymer scaffold line by line.

As shown in FIG. 4, bio-ink was printed on one side of the porous polymer scaffold using three-dimensional printing line by line.

More specifically, bio-ink containing a neuroregenerative material, neurotrophin (NGF) and collagen was printed to the porous polymer scaffold line by line.

Step 3: Wrapping the Porous Polymer Scaffold in a Conduit Form

Figure 5:
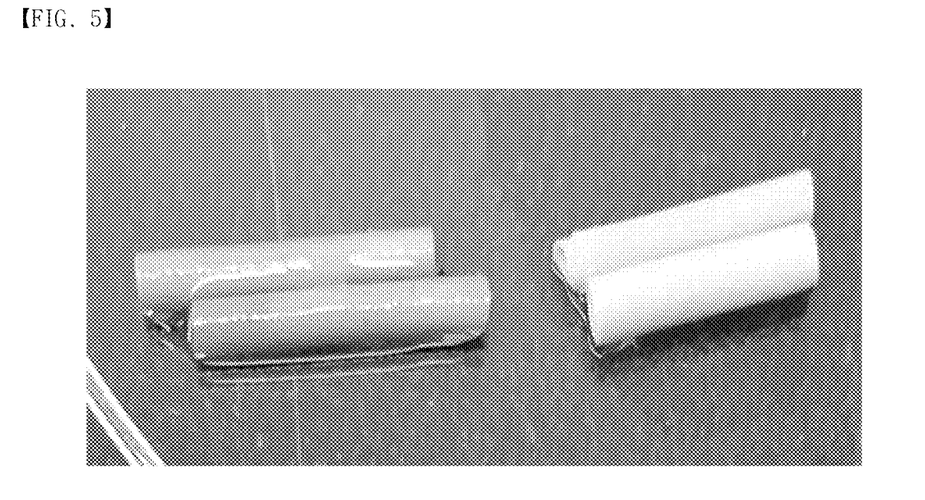
FIG. 5 is a photograph showing a nerve conduit containing neuroregenerative materials prepared in an example.

The bio-ink-printed porous polymer scaffold was wrapped in a conduit form to finally prepare a bio-printing nerve conduit containing a neuroregenerative material (See FIG. 5). FIG. 5 is a photograph showing the nerve conduit containing a neuroregenerative material prepared in the example.

Example 2. Preparation of a Nerve Conduit Using Bio-Printing Technology-2

Except that bio-ink containing collagen and decellularized tissue-derived hydrogel (dECM) was printed to the porous polymer scaffold line by line using three-dimensional printing, a nerve conduit was prepared by the same method as Example 1.

Experimental Example

Experimental Example 1. Structure Characteristics

Figure 6:
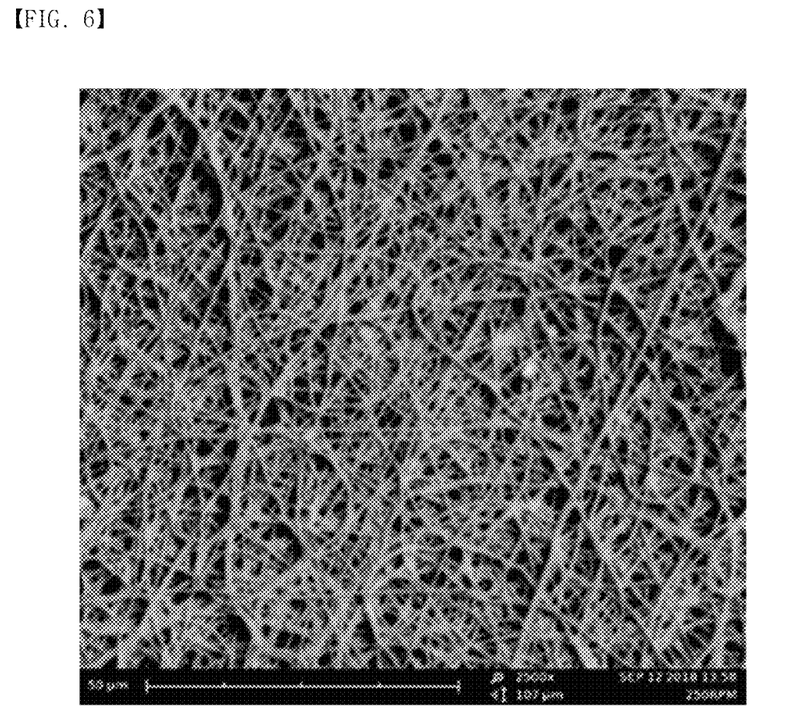
FIG. 6 is a photograph taking the porous polymer scaffold electrospun in an example of the present invention with an electron microscope.

To investigate the structure characteristics of the porous polymer scaffold prepared in Example 1, the surface of the scaffold was photographed with an electron microscope. Then, this was shown in FIG. 8.

FIG. 6 is a photograph taking the surface of the porous polymer scaffold electrospun in the example of the present invention with an electron microscope.

Referring to FIG. 6, it can be seen that the porous polymer scaffold has a structure in which fine fibers are layered, and has a structure in which nanofibers having a diameter of about 200 to 1000 nm are irregularly entangled. Through this, it can be seen that the porous polymer scaffold of the example of the present invention forms pores by that fine fibers are irregularly entangled.

Therefore, the nerve conduit according to the present invention is determined that the exchange of body fluids, substances and gases between the inside and outside of the conduit is easier compared to a nerve conduit prepared using a 3D printing mold, as the body fluid exchange between the inside and outside of the conduit is performed through the pores.

Experimental Example 2. Observation of the Survival Rate of Neurons

The survival rate of neurons of the nerve conduit prepared in the example was observed (7 days in vitro). Then, this was shown in FIGS. 7A and 7B.

Figure 7A:
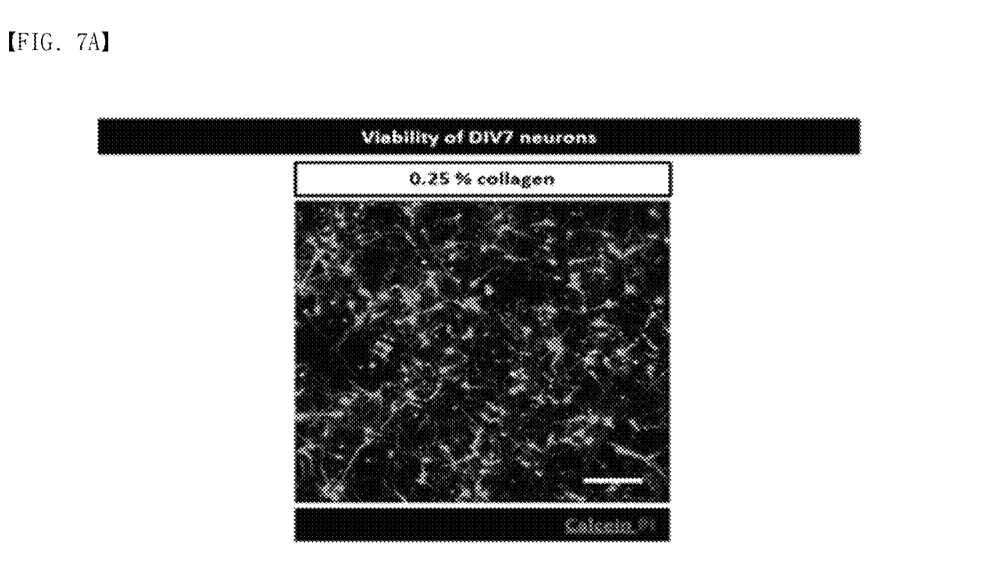
FIGS. 7A and 7B are drawings showing the result of growth of neurons (7A: 0.25% collagen, 7B: 0.25% collagen+0.1% dECM).
Figure 7B:
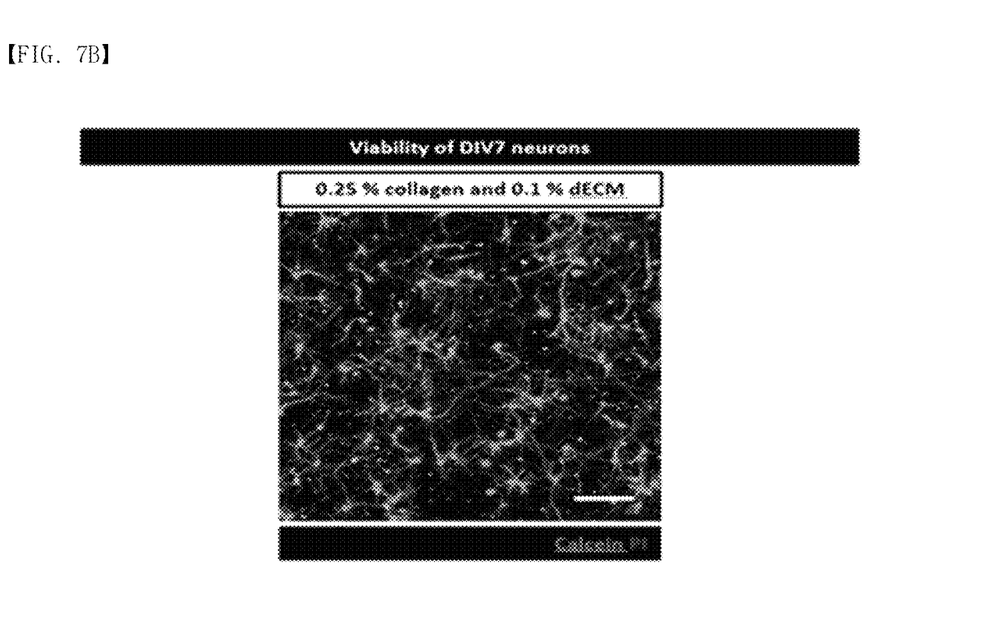

FIG. 7A is a drawing which shows the result of the growth of neurons in 0.25% collagen, and FIG. 7B is a drawing which shows the result of the growth of neurons in 0.25% collagen+0.1% dECM.

Referring to FIGS. 7A and 7B, it was confirmed that neurites of the neurons were developed in hydrogel containing a nerve-derived factor, and also networking between neurons formed a complex structure.

In particular, in case of decellularized tissue-derived hydrogel, it could be confirmed that neurons were differentiated and engrafted better in normal cells.

It is expected that the environment of hydrogel containing a nerve tissue-derived factor is effective in neuroregeneration.

The invention claimed is:

1. A method for preparing a nerve conduit, comprising
printing bio-ink on one side or both sides of a porous polymer membrane using a three-dimensional bio-printer (3D bio-printer); and
preparing a nerve conduit by wrapping the porous polymer membrane in which the bio-ink is printed in a conduit form;
wherein the bio-ink comprises a collagen hydrogel;
wherein the porous polymer membrane comprises poly(L-lactide-co-caprolactone); and wherein the bio-ink is printed in a plurality of lines in one direction.

2. The method for preparing a nerve conduit according to claim 1,
wherein the porous polymer membrane is wrapped into a tubular form, a winding form, or a fiber bundle form.

3. The method for preparing a nerve conduit according to claim 1,
A method for preparing a nerve conduit, comprising printing bio-ink on one side or both sides of a plurality of porous polymer membranes using a 3D bio-printer; stacking the plurality of porous polymer membranes; and wrapping the stacked plurality of porous polymer membranes in a multi-pipe form; wherein the bio-ink comprises a collagen hydrogel; and wherein the porous polymer membrane comprises poly(L-lactide-co-caprolactone).

4. The method for preparing a nerve conduit according to claim 1,
wherein the porous polymer membrane is in a sheet form obtained by electrospinning.

5. The method for preparing a nerve conduit according to claim 1,
wherein the collagen hydrogel further comprises a decellularized extracellular matrix (dECM) powder in an amount of 5% by weight or less based on the total weight of the collagen hydrogel.

6. The method for preparing a nerve conduit according to claim 1, wherein the bio-ink further comprises a neuroregenerative factor;
wherein the neuroregenerative factor is at least one selected from the group consisting of fibroblast growth factor (FGF), bone morphogenetic proteins (BMPs), granulocyte colony-stimulating factor (G-CSF), granulocyte-macrophage colony-stimulating factor (GM-CSF), epidermal growth factor (EGF), growth differentiation factor (GDF), insulin-like growth factor (IGF), interleukin (IL), migration-stimulating factor (MSF), macrophage-stimulating protein (MSP), neurotrophin (NGF), platelet-derived growth factor (PDGF), transforming growth factor (TGF), vascular endothelial growth factor (VEGF) and neurotrophic factor family (NTF).

7. The method for preparing a nerve conduit according to claim 1, wherein the bio-ink further comprises a cell;
wherein the cell is at least one selected from the group consisting of neurons and stem cells.

8. The method for preparing a nerve conduit according to claim 1,
wherein the bio-ink comprises a first bio-ink comprising a collagen hydrogel and a neurogenerative factor; and second bio-ink comprising a collagen hydrogel and a neuron.

9. The method for preparing a nerve conduit according to claim 1,
wherein the first bio-ink comprises a neuron, a neuroregenerative factor, and a collagen hydrogel; and the second bio-ink comprising a stem cell, a neuroregenerative factor, and a collagen hydrogel, wherein the neuroregenerative factor in the first bio-ink and the second bio-ink are different.

10. The method for preparing a nerve conduit according to claim 9,
wherein the three-dimensional bio-printer comprises at least two printing nozzles, and
the first bio-ink and the second bio-ink are printed by separate printing nozzles, respectively.

11. The method for preparing a nerve conduit according to claim 1,
further comprising applying an adhesive for biological tissue on the surface of the nerve conduit.

12. A nerve conduit prepared by the method of claim 1.

13. The nerve conduit according to claim 12,
wherein the nerve conduit is for central nerve or peripheral nerve regeneration.

* * * * *